US011896625B2

(12) United States Patent
Ishii et al.

(10) Patent No.: US 11,896,625 B2
(45) Date of Patent: *Feb. 13, 2024

(54) METHOD FOR PRODUCING THERAPEUTIC AGENT FOR SKIN LESIONS, AND THERAPEUTIC AGENT FOR SKIN LESIONS

(71) Applicant: WELL STONE CO., Miyazaki (JP)

(72) Inventors: Yoichi Ishii, Miyazaki (JP); Takeshi Okamoto, Miyazaki (JP); Sayaka Makino, Miyazaki (JP)

(73) Assignee: WELL STONE CO., Miyazaki (JP)

( * ) Notice: Subject to any disclaimer, the term of this patent is extended or adjusted under 35 U.S.C. 154(b) by 158 days.

This patent is subject to a terminal disclaimer.

(21) Appl. No.: 17/480,327

(22) Filed: Sep. 21, 2021

(65) Prior Publication Data

US 2022/0000937 A1 Jan. 6, 2022

Related U.S. Application Data

(63) Continuation of application No. 16/495,500, filed as application No. PCT/JP2018/010581 on Mar. 16, 2018, now Pat. No. 11,147,842.

(30) Foreign Application Priority Data

Mar. 21, 2017 (JP) ................. 2017-054774

(51) Int. Cl.
| | | |
|---|---|---|
| *A61K 36/62* | (2006.01) | |
| *A61K 35/62* | (2006.01) | |
| *A61K 35/02* | (2015.01) | |
| *A61P 17/02* | (2006.01) | |
| *A61K 9/12* | (2006.01) | |
| *A61K 36/13* | (2006.01) | |

(52) U.S. Cl.
CPC ................ *A61K 35/62* (2013.01); *A61K 9/12* (2013.01); *A61K 35/02* (2013.01); *A61K 36/13* (2013.01); *A61P 17/02* (2018.01)

(58) Field of Classification Search
None
See application file for complete search history.

(56) References Cited

U.S. PATENT DOCUMENTS

| | | |
|---|---|---|
| 2006/0035957 A1 | 2/2006 | Takeda et al. |
| 2009/0069307 A1 | 3/2009 | Takagi et al. |
| 2017/0348357 A1 | 12/2017 | Ishii et al. |
| 2019/0060215 A1 | 2/2019 | Ishii et al. |

FOREIGN PATENT DOCUMENTS

| | | |
|---|---|---|
| CN | 1684679 | 10/2005 |
| CN | 102144722 | 8/2011 |
| JP | 3779735 | 5/2006 |
| JP | 4961131 | 6/2012 |
| JP | 2012-197193 | 10/2012 |
| JP | 2013-180995 | 9/2013 |
| JP | 2015-93818 | 5/2015 |
| JP | 6100411 | 3/2017 |

OTHER PUBLICATIONS

International Search Report dated Apr. 17, 2018 in International Application No. PCT/JP2018/010581.
Kumar et al. (2013) Proc. Natl. Acad. Sci. India Sect. B. Biol. Sci. 83(2): 199-206. (Year: 2013).

*Primary Examiner* — Russell G Fiebig
(74) *Attorney, Agent, or Firm* — Wenderoth, Lind & Ponack, L.L.P.

(57) ABSTRACT

Provided are: a method of producing a therapeutic agent for skin lesions suitable for treatment or prevention of a skin lesion such as a bedsore; and a therapeutic agent for skin lesions produced by the production method. The method of producing a therapeutic agent for skin lesions characterized by including a mixing step of mixing earthworm castings with water and a collecting step of collecting vaporized water generated from a mixture obtained in the mixing step to obtain a liquid; and the therapeutic agent for skin lesions produced by the production method. It is preferred to further mix an organic substance together with the earthworm castings and the water in the mixing step.

4 Claims, No Drawings

METHOD FOR PRODUCING THERAPEUTIC AGENT FOR SKIN LESIONS, AND THERAPEUTIC AGENT FOR SKIN LESIONS

TECHNICAL FIELD

The present invention relates to: a method of producing a therapeutic agent for skin lesions suitable for treatment or prevention of a skin lesion such as a bedsore; and a therapeutic agent for skin lesions produced by the production method.

BACKGROUND ART

Conventionally, various therapeutic agents that can be used to treat a skin lesion such as a bedsore (or decubitus) have been studied (for example, Patent Documents 1 and 2), and generally, a therapeutic agent different from conventional ones is demanded due to difficulties in obtaining an effect depending on a target.

RELATED ART DOCUMENTS

Patent Document

Patent Document 1 JP 3779735B2
Patent Document 2 JP 4961131B2

SUMMARY OF THE INVENTION

Problems to be Solved by the Invention

In these situations, an object of the present invention is to provide: a method of producing a therapeutic agent for skin lesions suitable for treatment or prevention of a skin lesion such as a bedsore; and a therapeutic agent for skin lesions produced by the production method.

Means for Solving the Problems

The present inventors intensively studied to solve the above-described problems and consequently discovered that, a liquid obtained by collecting vaporized water generated upon mixing of earthworm castings with water is suitable for treatment or prevention of a skin lesion such as a bedsore, thereby completing the present invention.

Namely, a method of producing a therapeutic agent for skin lesions according to the present invention is characterized by including: a mixing step of mixing earthworm castings with water; and a collecting step of collecting vaporized water generated from a mixture obtained in the mixing step to obtain a liquid.

In the method of producing a therapeutic agent for skin lesions according to the present invention, it is preferred to further mix an organic substance together with the earthworm castings and the water in the mixing step.

In the method of producing a therapeutic agent for skin lesions according to the present invention, it is preferred that the organic substance is a wood material.

It is preferred that the method of producing a therapeutic agent for skin lesions according to the present invention further includes a diluting step of diluting the liquid obtained by the collection of the vaporized water in the collecting step with water.

A therapeutic agent for skin lesions according to the present invention is characterized by being produced by the method of producing a therapeutic agent for skin lesions.

It is preferred that the therapeutic agent for skin lesions according to the present invention is used in the form of mist.

It is preferred that the therapeutic agent for skin lesions according to the present invention is for treatment or prevention of a bedsore.

A method of treating a bedsore according to the present invention is characterized by administering the therapeutic agent for skin lesions to a patient.

It is preferred that the therapeutic agent for skin lesions according to the present invention is for use in the treatment of a bedsore.

Effects of the Invention

According to the present invention, it is possible to provide: a method of producing a therapeutic agent for skin lesions suitable for treatment or prevention of a skin lesion such as a bedsore; and a therapeutic agent for skin lesions produced by the production method.

Mode for Carrying Out the Invention

The method of producing a therapeutic agent for skin lesions according to the present invention is characterized by including: a mixing step of mixing earthworm castings with water; and a collecting step of collecting vaporized water generated from a mixture obtained in the mixing step. In the mixing step, it is preferred that an organic substance is further mixed together with the earthworm castings and the water. Although details about the mechanism is not known clearly, it is believed that microorganisms such as bacteria contained in earthworm castings decompose and ferment organic substances contained in the earthworm castings and organic substances added separately to the earthworm castings and, as a result, a liquid obtained by collecting the vaporized water is effective for treatment or prevention of a skin lesion such as a bedsore. Hereinbelow, the method of producing a therapeutic agent for skin lesions and the therapeutic agent for skin lesions according to the present invention will be described in detail.

[Therapeutic Agent for Skin Lesions Production Method]
(Mixing Step)

The mixing step is a step of mixing earthworm castings with water. The earthworm castings are not particularly limited, and castings of earthworms *Lumbricus rubellus*, *Lumbricus terrestris* (LT), *Eisenia foetida*, *Allolobophora caliginosa*, *Dendrobaena octaedra*, *Allolobophora japonica* Michaelsen, *Draw ida hattamimizu* Hatai, *Pheretima divergens* Michaelsen, *Pheretima communissima*, *Pheretima agrestis*, *Pheretima sieboldi* Horst, *Pheretima hilgendorfi*, *Pontodrilus matsushimensis* Iizuka, *Tubifex hattai* Nomura, and *Limnodrilus gotoi* Hatai (=*L. Socialis* Stephenson) can be used.

The water to be mixed with the earthworm castings is not particularly limited, and tap water and distilled water can be used. The water may be purified with a filtration material, a reverse osmosis membrane or the like. From the viewpoint of the removal of microorganisms such as bacteria, it is preferred to use a microporous filtration material, a microporous reverse osmosis membrane or the like. For example, an SPG (Shirasu porous glass) permeable membrane can be used preferably.

The mixing ratio of the earthworm castings and the water is preferably 0.05 to 20 L, more preferably 0.1 to 10 L, still more preferably 0.2 to 5 L, particularly preferably 0.5 to 2 L of the water with respect to 1 kg of the earthworm castings.

In the mixing step, it is preferred that an organic substance is further mixed together with the earthworm castings and the water. When an organic substance is mixed, a therapeutic agent for skin lesions excellent in the effect of treating or preventing a skin lesion can be produced, and the pH value of the therapeutic agent for skin lesions can be controlled. The organic substance is not particularly limited, as long as the organic substance can be decomposed when mixed with the earthworm castings. For example, an organic substance derived from a living organism such as an animal, a plant, a bacterium or a protozoan can be used. Specific examples of a plant-derived organic substance include: a wood material such as wood chips, wood dusts and rice hulls; a mushroom bed for use in the culturing of mushrooms; and the like. To mix a wood material as the organic substance is preferred, because an odorless liquid is likely to be collected in the collecting step. As the wood material, wood chips are preferred. The species of the wood is not particularly limited, and examples thereof include a conifer tree such as yew, Japanese torreya, Japanese cypress, hiba arborvitae, Japanese cedar, Japanese umbrella pine, pine, Japanese Douglas fir, hondo spruce, fir, hemlock fir, or sequoia, or a broadleaf tree such as Japanese cherry, oak, zelkova, beech, birch, chinquapin, maple, alder, Japanese linden, Japanese hornbeam, or bamboo. Among the wood, wood of *Pinales* can suitably be used. More preferably, wood of *Cupressaceae* can be used, still more preferably, wood of *Taxodioideae* can be used, and particularly preferably, wood of *Cryptomeria* can be used.

The mixing ratio of the earthworm castings and the organic substance is preferably 0.05 to 20 kg, more preferably 0.1 to 10 kg, still more preferably 0.2 to 5 kg, and particularly preferably 0.5 to 2 kg of the organic substance with respect to 1 kg of the earthworm castings.

The mixing method to be employed in the mixing step is not particularly limited, and it is preferred that the mixture is fully mixed by stirring or the like. The order in which the components are mixed is not particularly limited. For example, it is possible to introduce the earthworm castings and the organic substance into a vessel and subsequently add water thereto, and it is also possible to introduce the organic substance into a vessel, subsequently add water thereto, and subsequently add the earthworm castings thereto.

It is not necessary to mix the whole amounts of the components at once, but each of the water, the earthworm castings and/or the organic substance may be replenished in divided several portions during the mixing. To mix while replenishing is preferred, because it is possible to collect vaporized water continuously while replenishing the water that can be reduced by vaporization and the earthworm castings or the organic substance that can be reduced by decomposition.

In addition, the fermentation is further stabilized after a lapse of time from the first mixing procedure, and therefore, by collecting the vaporized water, for example, after a lapse of about 1 day, a liquid more excellent in an effect of treatment or prevention of a skin lesion can be obtained. From this view point, it is preferred to collect the vaporized water continuously while replenishing these components.

Heat is generated in the mixture as the result of the fermentation of the earthworm castings and the separately added organic substance. However, at some air temperatures, it is preferred to mix the components while warming. The warming may be carried out, for example, at 30 to 50° C.

(Collecting Step)

The collecting step is a step of collecting vaporized water generated from the mixture obtained in the mixing step to obtain a liquid (also referred to as "an aqueous organic substance decomposition product", hereinafter). The collecting step may be carried out while carrying out the mixing step.

In the collecting step, vaporized water generated in a temperature range rising due to a fermentation heat (reaction heat) generated as a result of the fermentation of the mixture can be collected, and it is not necessary to heat the mixture up to the boiling point. Depending on the temperatures, it is preferred to mix the components while warming. The warming may be carried out, for example, at 30 to 50° C.

The method of the collecting is not particularly limited, as long as vaporized water can be collected. For example, vaporized water may be collected with a dehumidifier. As the dehumidifier, a cooling-mode dehumidifier, a compression-mode dehumidifier or the like can be used. It is preferred to collect vaporized water without boiling the mixture.

The method of the conversion of the collected vaporized water to a liquid is not particularly limited. For example, when the vaporized water is collected with a dehumidifier, an aqueous organic substance decomposition product can be obtained. The dehumidifier is not particularly limited, as long as the vaporized water can be collected in a liquid form. For example, a cooling-mode dehumidifier, a compression-mode dehumidifier or the like can be used.

The pH value of the liquid obtained by the collection of the vaporized water is preferably 5 to 9, more preferably 6 to 8, still more preferably 6.5 to 7.5.

(Diluting Step)

The aqueous organic substance decomposition product obtained by the collection of the vaporized water in the collecting step may be used as a therapeutic agent for skin lesions without any modification. However, it is preferred to use the aqueous organic substance decomposition product in a diluted form. A solvent to be used for the dilution may be water, and tap water and distilled water can be used. The water to be used for the dilution may be purified with a filtration material, a reverse osmosis membrane and the like. From the viewpoint of the removal of microorganisms such as bacteria, it is preferred to use a microporous filtration material, a microporous reverse osmosis membrane or the like, and an SPG (Shirasu porous glass) permeable membrane is preferably used.

In the case where the aqueous organic substance decomposition product is diluted, the dilution may be carried out at a dilution factor of, for example, 1.5 to 10 folds, preferably 4 to 6 folds, more preferably 4.5 to 5.5 folds.

[Therapeutic Agent for Skin Lesions]

A therapeutic agent for skin lesions according to the present invention is characterized in that it is produced by the method of producing a therapeutic agent for skin lesions according to the present invention. The therapeutic agent for skin lesions according to the present invention is not particularly limited as long as the therapeutic agent for skin lesions is produced by the method of producing a therapeutic agent for skin lesions according to the present invention and is effective for treatment or prevention of a skin lesion such as a bedsore, and is preferably in a liquid form. Alternatively, the liquid therapeutic agent for skin lesions may be sprayed or evaporated in the form of a mist. Furthermore, the therapeutic agent for skin lesions may be processed into a solid form such as gel, powder, granule, sheet, or the like by mixing with, for example, an excipient or the like.

The therapeutic agent for skin lesions of the present invention may contain a pharmaceutically acceptable carrier. As a pharmaceutically acceptable carrier, an excipient, a binder, a disintegrant, a fluidizing agent, a lubricant, a coating agent, a suspending agent, a coloring agent, a sweetening agent, a surfactant, or the like can be used, and the composition can be made in the form of a general pharmaceutical preparation according to a known method. The composition may also contain another therapeutic/prophylactic ingredient or a pharmaceutically acceptable additive.

The blending amount of the liquid collected in the collecting step in the therapeutic agent for skin lesions of the present invention may be effectively determined depending on purposes. An appropriate blending amount depends on various factors such as purpose, form, production conditions, and the like, and for example, in the case of a liquid therapeutic agent for skin lesions, the amount of the liquid collected in the collecting step may be 5% by volume or more, preferably 5 to 50% by volume, more preferably 10 to 40% by volume, and still more preferably 20 to 30% by volume.

The amount of the therapeutic agent for skin lesions of the present invention to be used may also be an amount effective for the purpose. The appropriate amount to be used depends on various factors such as purpose, form, production conditions, and the like, and for example, when a liquid therapeutic agent for skin lesions is sprayed in the form of mist on an affected area, for example, five to six times per day and 10 to 15 mL per day may be used to the extent that the skin surface becomes wet.

The therapeutic agent for skin lesions of the present invention is preferably used for treatment or prevention of a skin lesion. The skin lesion is not particularly limited, and for example, the therapeutic agent for skin lesions of the present invention is favorably used for treatment or prevention of a bedsore.

In the therapeutic agent for skin lesions according to the present invention, other active ingredients and known conventional additives usable in therapeutic agent for skin lesions (e.g., a coloring agent, a fragrance, an antioxidant agent, an ultraviolet ray absorber, a chelating agent, a surfactant, a viscosity modifier, a pH modifier, a thickening agent, an antifoaming agent, a preservative agent, an bactericidal/antibacterial agent, a dispersant and an organic solvent) may be added, as long as the advantageous effects of the present invention cannot be deteriorated.

The therapeutic agent for skin lesions of the present invention may contain a dry powder, milled matter and/or extract of earthworm. By mixing a dry powder, milled matter, and/or extract of earthworm, it is possible to obtain a liquid more excellent in the effect of treatment or prevention of a skin lesion. Among these, an extract of earthworm is more preferable, since a more excellent effect can be obtained. As the earthworm extract, an extract produced by extracting a dried earthworm powder with water, ethanol or an aqueous ethanol solution can be used, for example.

Earthworms used as a raw material are not particularly limited, and, for example, *Lumbricus rubellus, Lumbricus terrestris, Eisenia foetida, Allolobophora caliginosa, Dendrobaena octaedra, Allolobophora japonica* Michaelsen, *Drawida hattamimizu* Hatai, *Pheretima divergens* Michaelsen, *Pheretima communissima, Pheretima agrestis, Pheretima sieboldi* Horst, *Pheretima hilgendorfi, Pontodrilus matsushimensis* Iizuka, *Tubifex hattai* Nomura, *Limnodrilus gotoi* Hatai (=*L. Socialis* Stephenson), or the like can be used.

The dry earthworm powder herein means a powder obtained by drying a milled matter or extract of untreated or pretreated earthworms. The milled matter of earthworms is a liquid or paste-like one obtained by milling untreated or pretreated earthworms. The extract of earthworms means an extract obtained by dissolving untreated or pretreated earthworms or milled matter thereof in water or an organic solvent, and by removing or separating an insoluble fraction. The pretreatment is not particularly limited, and examples thereof include a removal treatment of waste or the like described below. The dry powder, milled matter, and extract of earthworm may be subjected to post-treatment, and examples of the post-treatment include granulation, filtration, purification, concentration, dilution, and pH adjustment.

A milling method of obtaining the milled matter of earthworms is not particularly limited, and earthworms can be ground using a homogenizer, a blender, a homomixer, a grinder, a Dounce homogenizer, or the like.

An extracting method of obtaining the extract of earthworms is not particularly limited, and for example, the extraction can be obtained by dissolving a dry powder or milled matter of earthworms in an extraction solvent, and by removing or separating an insoluble fraction. Examples of the extraction solvent include water, an aqueous solution and an organic solvent such as ethanol, acetone, or ethyl acetate, and the extraction solvent may be used singly, or two or more types thereof may be used in combination. Among them, water, ethanol, or aqueous ethanol solution is preferable.

A drying method of obtaining dried earthworms is not particularly limited, and the dried earthworms can be obtained by a drying method such as freeze drying, heat drying, or spray drying. Among them, freeze drying is preferred for the reasons described below.

It is preferable to remove digestive substances remaining in the gastrointestinal tract of earthworms, wastes adhering to the body surface of earthworms, and the like. The removal method is not particularly limited, and a known method may be used for removal. For example, a method in which earthworms are immersed in an aqueous solution of an alkaline salt such as sodium salt or potassium salt to excrete loess in the gastrointestinal tract (a method described in JP Nos. H01-47718A, H01-47719A, H01-47720A, or H01-268639A), a method in which earthworms are allowed to stand in an acid aqueous solution maintained at 6 to 26° C. for 0.1 to 5 hours to remove feces from the gastrointestinal tract (a method described in JP No. H03-72427A), or the like may be employed.

In the removal method, it is preferable to bring earthworms into contact with the following metal chloride and/or hydroxycarboxylic acid.

The chloride of the above-described metal is a chloride of at least one metal selected from the group consisting of potassium, sodium, magnesium, and calcium. In other words, the chloride of metal is at least one selected from the group consisting of potassium chloride, sodium chloride, magnesium chloride, and calcium chloride. A mixture of these or a mixture of these and other harmless components that can be added to food may be used. Examples of such a mixture include salt, rock salt, and solar salt. A chloride of the above-described metal can be used by sprinkling in a powdery form on living earthworms, whereby the earthworms are in contact with the metal chloride.

It is preferable to bring living earthworms into contact with hydroxycarboxylic acid as described below after bringing the living earthworms into contact with a chloride of the above-described metal. It is also possible to bring the earthworms into contact with hydroxycarboxylic acid as described below without being in contact with a chloride of the above-described metal.

The above-described contact with hydroxycarboxylic acid can also be carried out by sprinkling powdery hydroxycarboxylic acid on living earthworms. The living earthworms may be immersed in a hydroxycarboxylic acid aqueous solution having a pH of 2 to 5. When bringing into contact with hydroxycarboxylic acid after being in contact with a metal chloride, it is preferable that the contact with hydroxycarboxylic acid is carried out promptly after contact with the chloride of the above-described metal. It is preferable to wash living earthworms before bringing the living earthworms into contact with hydroxycarboxylic acid. When the earthworms and hydroxycarboxylic acid are brought into contact with each other after removing the chloride of the above-described metal by washing with water, an earthworm dry powder having high enzyme activity is obtained. In the case of washing with water prior to contact with hydroxycarboxylic acid, washing is carried out preferably within 30 minutes, more preferably within 20 minutes after the start of contact with the metal chloride. The washing method is not particularly limited, and a known method can be adopted.

When living earthworms are brought into contact with hydroxycarboxylic acid powder for a long time, they die, they lose their living functions, and do not excrete digestive substances in the gastrointestinal tract, and therefore, it is preferable to adjust the pH to 2 to 5 by diluting the hydroxycarboxylic acid with water as soon as possible, preferably within 30 seconds, more preferably within 20 seconds.

Because hydroxycarboxylic acid forms an unpleasant living environment for earthworms, living earthworms try to improve the living environment by releasing body fluids and excreta by self-preservation instinct. Since hydroxycarboxylic acid has bactericidal properties, hydroxycarboxylic acid plays a role of promoting excretion of digestive substances and the like remaining in the digestive organs as described above, and hydroxycarboxylic acid can be expected to have an effect of sterilizing germs attached to earthworms.

The crystalline hydroxycarboxylic acid used in the above-described method can be used irrespective of the number of hydroxy groups or the number of carboxyl groups as long as the crystalline hydroxycarboxylic acid shows a crystalline form under the conditions of use. In other words, any of monohydroxy monocarboxylic acid, monohydroxy polycarboxylic acid, polyhydroxy monocarboxylic acid and polyhydroxy polycarboxylic acid may be used.

Examples of the hydroxycarboxylic acid include glycolic acid, lactic acid, acetic acid, β-hydroxypropionic acid, α-hydroxy-n-butyric acid, β-hydroxy-n-butyric acid, α-hydroxy-n-valeric acid, β-hydroxy-n-valeric acid, malic acid, α-methyl malic acid, α-hydroxy glutaric acid, β-hydroxy glutaric acid, citric acid, malonic acid, and succinic acid. Among them, lactic acid, acetic acid, malic acid, citric acid, malonic acid, and succinic acid are preferable because they can be used for food and are easily available. The hydroxycarboxylic acid may be used singly, or two or more kinds thereof may be used in a mixture.

Water accounts for 65% of the tissues of a living earthworm. There is a margin for the time until the life-keeping function of a living earthworm works, but as the living earthworm dies, an enzyme works, and therefore, it is necessary to carefully control the time to put the living earthworm in an uncomfortable living environment. Although this time depends on conditions, it is usually in a range of 3 to 180 minutes.

It is preferable that a living body of earthworm treated with hydroxycarboxylic acid is washed with water and then milled to obtain a liquid or pasty milled matter. Washing is preferably performed with pure water. The washing method is not particularly limited, and a known water washing method can be adopted. The total time of a treatment process before milling, or the time until cleaning of hydroxycarboxylic acid with water by sprinkling metal chloride on the living earthworms is preferably within a total of 240 minutes.

The above-described milling method is not particularly limited, and for example, milling is carried out usually at 1 to 25° C., for example, using a homogenizer, a blender, a homomixer, a grinder, a Dounce homogenizer. From the viewpoint of suppressing decomposition of earthworm constituents, it is preferable to carry out the milling at low temperature, and a temperature of 2 to 15° C. is preferable.

A milled matter obtained by milling earthworms are contained in, for example, a stainless steel tray, and subjected to freeze drying. At this time, an enzyme contained in a living body of earthworm does not act on living cells, but acts instantaneously on dead cells, and as a result, a putrefactive gas may be generated. In order to prevent this, it is preferable to instantaneously quench and freeze to −18° C. to −35° C. to suppress the action of the enzyme and then perform freeze-drying.

As described above, it is preferable to quickly freeze earthworms in order to make the earthworms into a powder without impairing the original pharmacological action of the earthworms, and on the other hand, when the earthworms are frozen in a very short time, impurities that are present together with protein, which is the main component of an earthworm paste, form a spot-like unfrozen part, and may not be separated, and therefore, excessively rapid freezing is not preferable. Therefore, freezing is preferably carried out at a low temperature of −18° C. to −35° C. for 20 to 240 hours, and more preferably 50 to 170 hours.

When performing freeze-drying, it is important to choose the conditions under which moisture and impurities can be removed without remaining. For that purpose, it is preferable to carry out freeze-drying at a temperature of −60° C. to +90° C. under a pressure of 50 Pa or lower while controlling the temperature stepwise in the range of 10 to 60 hours.

In a method of freeze-drying, for example, as described above, a milled matter is frozen at a temperature of −18° C. to −35° C. for 20 to 240 hours, the temperature is then raised in several steps at a temperature of −60° C. to +90° C., and the milled matter is frozen vacuum dried for 10 to 60 hours while reducing pressure in several stages at a pressure of 25 to 40 Pa, whereby a light yellow earthworm dry powder in a sterile state can be obtained.

Furthermore, it is preferable to include a step of dissolving the milled matter in a freeze-dried form in water or an aqueous ethanol solution and removing or separating an insoluble fraction. A step of removing or separating an insoluble fraction can be carried out by precipitation, centrifugation, filtration, or the like by standing as in the above. A step of dissolving in water or an aqueous ethanol solution is preferably carried out with stirring or shaking. Time required for dissolution in water is preferably 1 to 120 minutes, and more preferably 5 to 80 minutes. The ethanol concentration of the aqueous ethanol solution is not particularly limited, and is preferably 10 to 70% (v/v), and more preferably 30 to 60%.

A supernatant obtained by dissolving an earthworm extract in water or an aqueous ethanol solution as described above may be used as it is in the form of an aqueous solution, may be used as a concentrate after removing water, or may also be used in the form of powder by drying. A powder obtained by drying the supernatant may be dissolved in water and used. Alternatively, a powder obtained by freeze-drying an earthworm paste may be used as it is without being dissolved in water or an aqueous ethanol solution.

In the removal method, prior to a process of placing living earthworms in an unpleasant environment, or before bringing the living earthworms into contact with metal chloride or hydroxycarboxylic acid, it is preferable that the living earthworms are transferred to a flat box like a bread box, and that the living earthworms are left in a light place for 10 to 50 hours to remove a waste adhering to the body skin. The standing time in the light place is more preferably 12 to 24 hours. The amount to be accommodated at this time is preferably such an amount that the earthworms are stacked in a thickness of 30 to 60 mm, and preferably 40 to 50 mm. It is preferable that there is no foreign matter such as sand or mud in this flat box, and since earthworms are nocturnal, living activities become active in dark places and earthworms may consume physical strength, and therefore, keeping the interior of the box bright at night using an electric light culture method is preferable. By this treatment, the living earthworm exerts self-defense instinct, excretes digestive substances remaining in the gastrointestinal tract, covers the entire body with these excreta, prevents evaporation of moisture, and tries to maintain the living environment, and therefore, by repeatedly peeling off the covered wastes or excreta by appropriate means, it is possible to finally eliminate digestive substances in the gastrointestinal tracts and the wastes adhering to the body surface of the earthworms.

Peeling off of wastes adhering to the body surface of earthworms can be carried out, for example, by covering the living earthworms with a nonwoven fabric and adsorbing the wastes on the fabric. By combining: standing the earthworms in this light place and removing the wastes adhering to the body surfaces; and bringing the living earthworms into contact with the above-described metal chloride and/or hydroxycarboxylic acid, toxic substances are further expected to be discharged or removed from the earthworms.

As a method of obtaining a dry earthworm powder, the following methods are preferable particularly from the viewpoint of storage stability of the dry powder.
(A-1) A method of producing a dry earthworm powder including the steps of:
bringing a living earthworm into contact with at least one metal chloride selected from the group consisting of potassium, sodium, magnesium, and calcium,
subsequently bringing the living earthworms into contact with a powdery hydroxycarboxylic acid, diluting the earthworms with water to adjust the pH to 2 to 5, after holding the earthworms for 3 to 180 minutes, washing the earthworm with water, milling the earthworm, and freeze drying the obtained milled matter.
(A-2) A method of producing a dry earthworm powder including the steps of:
bringing living earthworms into contact with at least one metal chloride selected from the group consisting of potassium, sodium, magnesium, and calcium,
subsequently immersing the living earthworms in a hydroxycarboxylic acid aqueous solution in which the pH is adjusted to 2 to 5, holding the earthworms for 3 to 180 minutes, washing the earthworms with water, milling the earthworms, and freeze drying the obtained milled matter.
(A-3) A method of producing a dry earthworm powder further including in the (A-1) or (A-2) the steps of: dissolving the milled matter in a freeze dried form in water or an aqueous ethanol solution, removing or separating an insoluble fraction, and again performing freeze drying.

After freeze-drying the milled matter obtained by grinding the living earthworms, the dried product obtained may be heat-treated from the viewpoint of sterilization of the dried product. The temperature of the heat treatment is preferably 110° C. or more and less than 130° C. When the heating temperature is lower than 110° C., sterilization of the dried product may be insufficient, and when the heating temperature is 130° C. or higher, an enzyme contained in the dried earthworm product is deactivated and the activity is unfavorably lowered. More preferably, the heating temperature is 115 to 125° C. The heating method is not particularly limited, and examples thereof include a method of applying hot air, a method of using a heating jacket, a method of heating on a tray or the like, a method of heating with a heater, and a method using a constant temperature thermostat. The heating time is preferably 30 seconds to 130 minutes, more preferably 30 minutes to 90 minutes, and still more preferably 60 minutes to 90 minutes. When the heating time is too short, sterilization may be insufficient, and when the heating time is too long, the activity of the enzyme will be lost, which is not preferable. Since the enzymatic activity is lost when the enzyme in the liquid is subjected to the heat treatment, it is preferable to perform the heat treatment on the dry earthworm powder.

As a method of obtaining a milled matter of earthworms, the following methods are preferable.
(B-1) A method of producing a milled matter of earthworms including the steps of:
bringing living earthworms into contact with at least one metal chloride selected from the group consisting of potassium, sodium, magnesium, and calcium,
subsequently bringing the living earthworms into contact with a powdery hydroxycarboxylic acid, diluting the earthworm with water to adjust the pH to 2 to 5, after holding the earthworm for 3 to 180 minutes, washing the earthworms with water, and milling the earthworm.
(B-2) A method of producing a milled matter of earthworms including the steps of:
bringing living earthworms into contact with a metal chloride selected from the group consisting of potassium, sodium, magnesium, and calcium,
subsequently immersing the living earthworms in a hydroxycarboxylic acid aqueous solution in which the pH is adjusted to 2 to 5, holding the earthworms for 3 to 180 minutes, washing the earthworm with water, and milling the earthworms.

As a method of obtaining an extract of earthworms, the following methods are preferable.
(C-1) A method of producing an extract of earthworms including the steps of:
bringing living earthworms into contact with at least one metal chloride selected from the group consisting of potassium, sodium, magnesium, and calcium,
subsequently bringing the living earthworms into contact with a powdery hydroxycarboxylic acid, diluting the earthworms with water to adjust the pH to 2 to 5, after holding the earthworms for 3 to 180 minutes, washing the earthworm with water, milling the earthworms, dissolving the obtained milled matter in a freeze dried form in water of an aqueous ethanol solution, and removing or separating an insoluble fraction.

(C-2) A method of producing an extract of earthworms including the steps of:

bringing living earthworms into contact with a metal chloride selected from the group consisting of potassium, sodium, magnesium, and calcium, subsequently immersing the living earthworms in a hydroxycarboxylic acid aqueous solution in which the pH is adjusted to 2 to 5, holding the earthworms for 3 to 180 minutes, washing the earthworm with water, milling the earthworms, dissolving the obtained milled matter in a freeze dried form in water of an aqueous ethanol solution, and removing or separating an insoluble fraction.

Although the blending amount of a dry powder, milled matter, and/or extract of an earthworm is not particularly limited, in the case of a liquid therapeutic agent for skin lesions, for example, the blending amount is, per 100 L of the therapeutic agent for skin lesions in terms of dry mass of the extract extracted with water, 0.1 to 100 mg, preferably 0.2 to 50 mg, and more preferably 1 to 20 mg.

EXAMPLES

Hereinbelow, the present invention will be described more specifically with reference to Examples. However, the present invention is not intended to be limited by the following Examples. In the following Examples, "percent (%)" is by mass unless otherwise specified.

(Aqueous Organic Substance Decomposition Product)

Forty liters of water was introduced into a reaction vessel containing 40 kg of earthworm Lumbricus rubellus castings and 15 kg of a wood material (Japanese cedar) (5 kg of woodchips and 10 kg of a blend of wood dusts and rice hulls), and then vaporized water was collected by a dehumidifier (DM-30, manufactured by NAKATOMI Corporation) attached to the reaction vessel for about 1 day while stirring to obtain 15 to 20 L of a liquid. Ten to twenty liters of water was further added to the reaction vessel, then 10 kg of a wood material (Japanese cedar) (5 kg of woodchips and 5 kg of a blend of wood dusts and rice hulls) was added thereto, and then vaporized water was collected by the dehumidifier for about 1 day in the same manner to obtain 15 to 20 L of a liquid. About 40 L of a liquid (pH 8.71) prepared by mixing the obtained liquids was used as an aqueous organic substance decomposition product.

In the production of the above-described aqueous organic substance decomposition product, the water used was water prepared by purifying tap water with an SPG (Shirasu porous glass) permeable membrane (SPG Technology Co., Ltd.) and activated carbon.

(Earthworm Extract)

After standing for 24 hours in a light place, 30 kg of living Lumbricus rubellus of which a waste was peeled from the body skin was spread out to about 5 cm in the thickness on a flat plate, and 250 g of sodium chloride was evenly sprinkled on top of this. After 20 minutes, the earthworms were washed with water. Thereafter, 250 g of citric acid was sprinkled in the same manner, and then the earthworms were diluted by adding 30 liters of pure water in 15 seconds. At this time, the pH immediately after addition of water was 2.25, and the pH when completely diluted was 2.74. When sprinkled with citric acid powder, the earthworms released yellow body fluid at once. After dilution with water, the earthworms were kept for 20 minutes in that state. Subsequently, the living earthworms were taken out from the soiled citric acid aqueous solution, washed with water, and milled at 10° C. using a homogenizer to prepare an earthworm paste. Next, the earthworm paste was suctioned and deaerated, a gas contained therein was removed, and the paste was then transferred to a stainless steel tray, instantaneously cooled to −35° C., and gradually frozen while maintaining this temperature for 50 hours. The frozen earthworm paste was kept at −35° C. and 0 Pa for 2 hours, the temperature was then raised to 25° C. at 40 Pa for 10 hours, the temperature was then raised to 40° C. at 35 Pa for 14 hours, the temperature was then raised to 65° C. at 35 Pa for 12 hours, and finally, the temperature was raised to 80° C. at 25 Pa for 6 hours to perform vacuum freeze drying. By this treatment, a light yellow dry earthworm powder having a water content of 8% by mass was obtained.

25 g of the dry earthworm powder obtained as above was sampled, 500 mL of distilled water was added thereto, and the mixture was stirred and extracted at room temperature for 1 hour. The obtained extract was centrifuged (10,000×g, 4° C., 15 minutes), a supernatant was collected, and an earthworm extract was obtained. The obtained extract was finely pulverized with a freeze vacuum dryer, 30 mg was sampled, and diluted with 500 mL of distilled water to obtain a stock solution.

(Therapeutic Agent for Skin Lesions)

The aqueous organic substance decomposition product obtained above was diluted 5-fold with water. The water used for dilution was water prepared by purifying tap water with an SPG (Shirasu porous glass) permeable membrane (SPG Technology Co., Ltd.) and activated carbon.

The diluted aqueous organic substance decomposition product and the diluted stock solution of the earthworm extract obtained above were mixed at a ratio of 1,000:1 and passed through a 0.2 µm filter to obtain a therapeutic agent for skin lesions.

Example 1

<Bedsore 1>

The therapeutic agent for skin lesions obtained above was sprayed in the form of mist on an affected area of the subject below daily for 5 to 6 times a day at a volume of about 2 mL, and symptoms of a bedsore were observed.

Subject: Male, 75 years old, History of the symptoms: 3 years, Odor of the affected part: strong After 7 days, odor, oozing, and itching decreased.

After 15 days, odor and itching disappeared. Oozing reduced.

After 25 days, back to normal skin.

Example 2

<Bedsore 2>

The therapeutic agent for skin lesions obtained above was sprayed in the form of mist on an affected area of the subject below daily for 5 to 6 times a day at a volume of about 2 mL, and symptoms of a bedsore were observed.

Subject: Female, 80 years old, History of the symptom: 2 years, Odor of the affected part: strong After 7 days, odor, oozing, and itching decreased.

After 10 days, odor and itching disappeared. Oozing reduced.

After 20 days, back to normal skin.

As shown in Examples 1 and 2, it can be seen that a therapeutic agent for skin lesions suitable for treating or preventing a skin lesion can be produced by collecting evaporated water generated from a mixture of earthworm castings and water.

The invention claimed is:

1. A method of producing a therapeutic agent for skin lesions comprising the steps of:
   (a) mixing earthworm castings with water to obtain a mixture while warming at 30 to 50° C.;
   (b) vaporizing the mixture to generate a vaporized water; and
   (c) collecting the vaporized water generated from the mixture to obtain a liquid containing the therapeutic agent.

2. The method according to claim 1, further comprising mixing an organic substance together with the earthworm castings and the water in the mixing step.

3. The method according to claim 2, wherein the organic substance is a wood material.

4. The method according to claim 1, further comprising a diluting step of diluting the liquid obtained in the collecting step with water.

\* \* \* \* \*